United States Patent [19]
Shimamura et al.

[11] Patent Number: 5,807,564
[45] Date of Patent: Sep. 15, 1998

[54] METHOD OF STRENGTHENING ANTIBACTERIAL ACTION OF ANTIBIOTICS

[75] Inventors: Tadakatsu Shimamura, Tokyo; Yukihiko Hara, Fujieda, both of Japan

[73] Assignee: Mitsui Norin Co., Ltd., Tokyo, Japan

[21] Appl. No.: 649,819

[22] Filed: May 17, 1996

[30] Foreign Application Priority Data

Sep. 6, 1995 [JP] Japan ................................. 7-252039
Mar. 5, 1996 [JP] Japan ................................. 8-073104

[51] Int. Cl.$^6$ .................................................. A01N 25/32
[52] U.S. Cl. ...................... 424/406; 424/405; 424/195.1; 514/456
[58] Field of Search ................................ 424/405, 406, 424/195.1; 514/453, 456, 460; 560/68; 435/177

[56] References Cited

U.S. PATENT DOCUMENTS 5,358,713  10/1994  Shimamura ............................ 424/195.1

FOREIGN PATENT DOCUMENTS 0 443 090  8/1991  European Pat. Off. .
40 26 683  2/1992  Germany .
WO 95/23607  9/1995  WIPO .

OTHER PUBLICATIONS

Patent Abstracts of Japan, vol. 960, No. 001 of JP–8026991 (Kureha Chem. Ind. Co., Ltd.), Jan. 30, 1996.
Database WPI, Week 9614, Derwent Publications Ltd., London, GB; AN 96–136179 of JP–8026991, (Kureha Chem. Ind. Co., Ltd.), Jan. 30, 1996.
USPDI, Ninth Edition, 1989 vol. IA; p. 130, Amino Glycoider.

*Primary Examiner*—Neil S. Levy
*Attorney, Agent, or Firm*—Frishauf, Holtz, Goodman, Langer & Chick, P.C.

[57] ABSTRACT

A method of increasing the activity of an antibiotic against methicillin resistant *Staphylococcus aureus* in a patient by administering to the patient the antibiotic in combination with a catechin and/or a theaflavin.

14 Claims, 8 Drawing Sheets

METHOD OF STRENGTHENING ANTIBACTERIAL ACTION OF ANTIBIOTICS

FIELD OF THE INVENTION

The present invention relates to a method of strengthening the antibacterial action of antibiotics. More specifically, the present invention relates to a method of strengthening the antibacterial action of antibiotics against methicillin resistant *Staphylococcus aureus* (abbreviated hereinafter as MRSA) by the combined use of the antibiotics with a tea catechin and/or theaflavin.

BACKGROUND INFORMATION

With the popularization and rapid development of medical treatments, various kinds of antibiotics are being used in the medical world. However, bacteria resistant to these antibiotics have emerged, and MRSA is representative of such.

MRSA shows resistancy to not only methicillin, but to most medications and since up until now there has been no conclusively effective treatment, arbekacin or vancomycin is at present being used in combination with other medications. However, this kind of combination treatment requires the intake of many kinds of medications in large amounts, and thus presents problems such as the increased possibility of detrimental side-effects. So with the increase in "compromised hosts" a method of controlling MRSA is urgently required.

The present inventors have shown and reported that tea extractions and tea catechins in clinical use show an antibacterial action against MRSA isolate (Jpn. J. Bacteriol., 46, 839–845, 1991). For example, administration of 250 mg/ml of epigallocatechin gallate showed an antibacterial action against MRSA, and within 24 hours $10^4$ cells/ml of MRSA were destroyed. We have also reported that tea catechins combined with exotoxin, for example α-toxin of *Staphyloccus aureus*, and rendered them inactive (Jpn. J. Bacteriol.,45, 561–566, 1990; Jpn. J. Bacteriol.,45, 913–919, 1990.).

Further, a method of preventing the transmission of infection caused by MRSA with the use of tea polyphenols is disclosed in U.S. Pat. No. 5,358,713.

SUMMARY OF THE INVENTION

A method of increasing activity of an antibiotic against methicillin resistant *Staphylococcus aureus* in a patient in need thereof, comprising administering to said patient an effective antibiotic amount of said antibiotic in combination with a synergistic amount of at least one polyphenol selected from the group consisting of a catechin of the following formula (I) and/or a theaflavin of the following formula (II).

DETAILED DESCRIPTION OF THE PREFERRED EMBODIMENTS

Figure 1A:
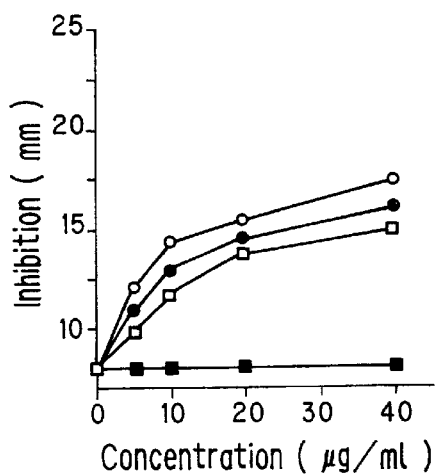
FIG. 1A is a graph which shows synergistic effect of tea catechin (Polyphenon 100) with oxacillin against MRSA strain H-5.
Figure 1B:
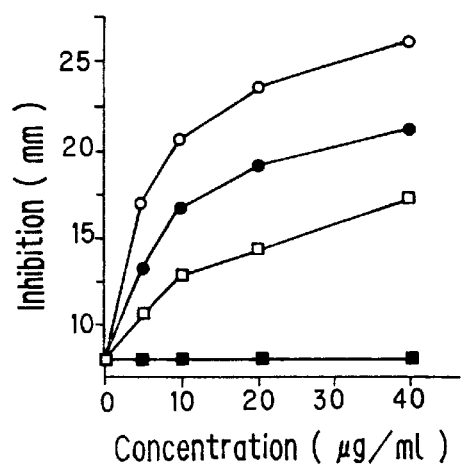
FIG. 1B is a graph which shows the synergistic effect of tea catechin (Polyphenon 100) with oxacillin against MRSA strain H-8.
Figure 1C:
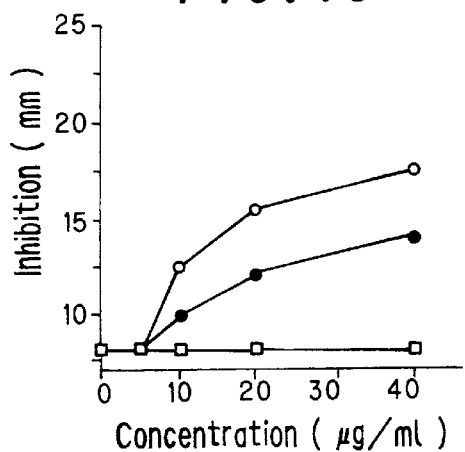
FIG. 1C is a graph which shows the synergistic effect of tea catechin (Polyphenon 100) with oxacillin against MRSA strain H-13.
Figure 1D:
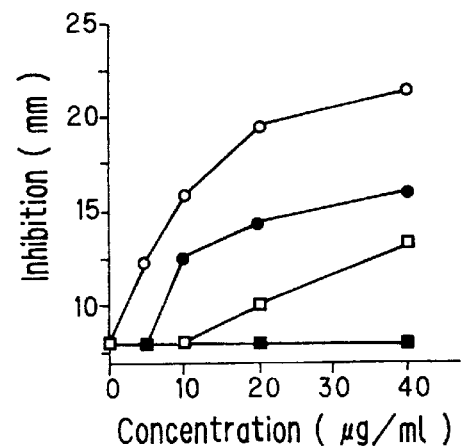
FIG. 1D is a graph which shows the synergistic effect of tea catechin (Polyphenon 100) with oxacillin against MRSA strain H-18.
Figure 1E:
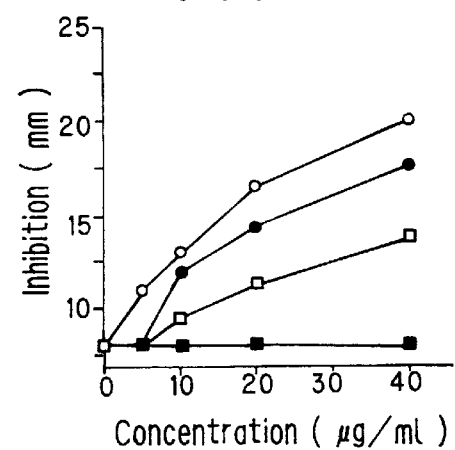
FIG. 1E is a graph which shows the synergistic effect of tea catechin (Polyphenon 100) with oxacillin against MRSA strain 21.
Figure 1F:
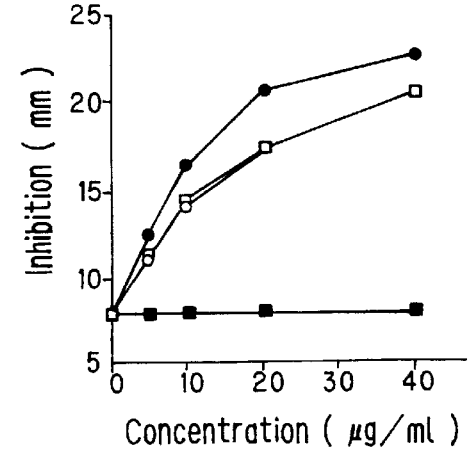
FIG. 1F is a graph which shows the synergistic effect of tea catechin (Polyphenon 100) with oxacillin against MRSA strain H-28.
Figure 2A:
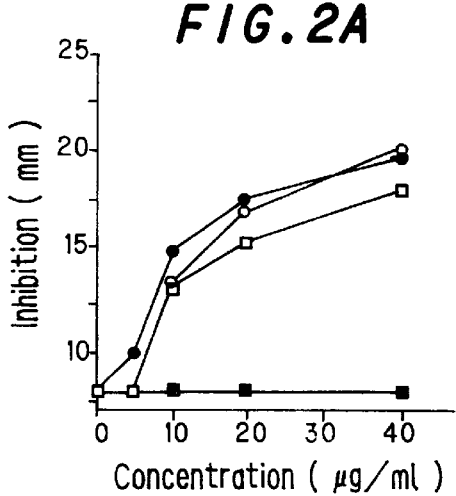
FIG. 2A is a graph which shows the synergistic effect of tea catechin (Polyphenon 100) with oxacillin against MRSA strain F-8.
Figure 2B:
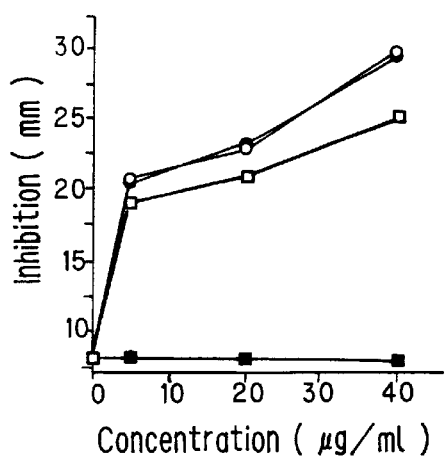
FIG. 2B is a graph which shows the synergistic effect of tea catechin (Polyphenon 100) with oxacillin against MRSA strain F-10.
Figure 2C:
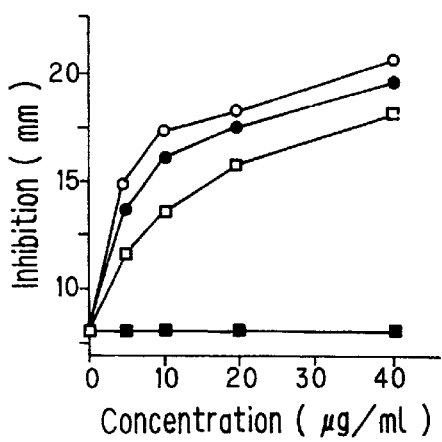
FIG. 2C is a graph which shows the synergistic effect of tea catechin (Polyphenon 100) with oxacillin against MRSA strain F-49.
Figure 2D:
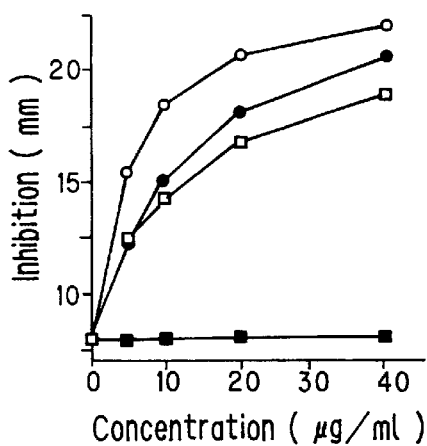
FIG. 2D is a graph which shows the synergistic effect of tea catechin (Polyphenon 100) with oxacillin against MRSA strain F-68.
Figure 2E:
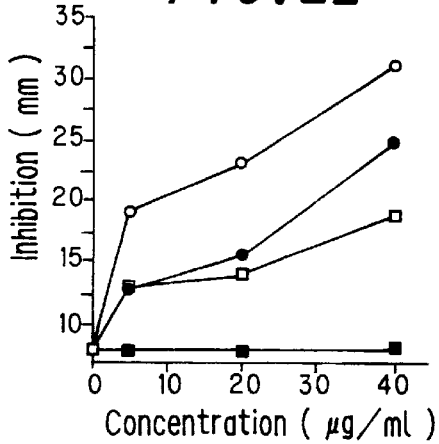
FIG. 2E is a graph which shows the synergistic effect of tea catechin (Polyphenon 100) with oxacillin against MRSA strain F-74.
Figure 2F:
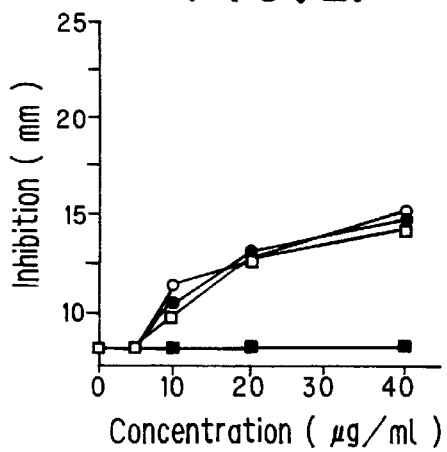
FIG. 2F is a graph which shows the synergistic effect of tea catechin (Polyphenon 100) with oxacillin against MRSA strain F-96.

The present inventors conducted an oxacillin antibacterial test using the orthodox cup method on a clinical MRSA isolate and found that when less than the minimum inhibitory concentration (MIC) of tea catechins (25–100 μg/ml) was added to the agar plate, oxacillin showed an antibacterial action on all of the MRSA isolates and the MIC was 5–12.5 μg/ml. However, without the addition of tea catechins, even a concentration of 40 μg/ml oxacillin had no antibacterial action.

Next, by counting the number of viable cells at intervals we observed the antibacterial action against MRSA when tea catechins and oxacillin were added simultaneously. When oxacillin was added independently (5 μmg/ml), no antibacterial effect was confirmed and the same growth curve as the control was observed; whereas when tea catechins (100 μmg/ml) were added with oxacillin, a synergistic effect was apparent and after 24 hours the viable cells had decreased to 1/100–1/10000.

These results demonstrate that the combination of tea catechins with oxacillin has a synergistic effect and it was confirmed that tea catechins stimulate the antibacterial action of oxacillin against MRSA. The same effect was observed when theaflavins were used instead of tea catechins.

Further, the influence of tea catechins on the antibacterial action of each kind of antibiotic to which MRSA showed resistancy was measured using the cup method as described above. Results showed that when 100 μg/ml of tea catechin were combined with specific antibiotics, i.e. methicillin (12.5 μg/ml), aminobenzyl penicillin (32 μg/ml), tetracycline (2.5 μg/ml) or chloramphenicol (12.5 μg/ml), these antibiotics had an antibacterial action on MRSA, and thus the effectiveness of tea catechins when used in combination with antibiotics other than oxacillin was confirmed.

According to these investigations it was found that when antibiotics which showed no antibacterial action on MRSA when used independently, were used in conjunction with tea catechins and/or theaflavins in a concentration less than the MIC, there was an apparent antibacterial action on MRSA.

On the basis of these discoveries the present inventors developed and completed a method of strengthening the antibacterial action of antibiotics against MRSA.

Thus the present invention relates to a method of increasing the antibacterial action of antibiotics against MRSA in a patient in need thereof, comprising administering to said patient an effective antibiotic amount of said antibiotic in combination with a synergistic amount of at least one polyphenol selected from the group consisting of a catechin of the following formula (I) and/or a theaflavin of the following formula (II).

The antibiotics used in the present invention showed no antibacterial action against MRSA when used independently. Antibiotics such as these include β-lactum type, aminoglycoside type etc., and more specifically, oxacillin, methicillin, aminobenzyl penicillin, cephalexin, penicillin G, amikacin, tetracycline, chloramphenicol, gentamicin and the like are illustrated as such antibiotics.

Out of these antibiotics, for example, oxacillin had a MIC of more than 1000 μg/ml against MRSA.

In the present invention, the antibiotics are used in such a small amount that they would not be effective against MRSA if used independently. Usually, 2 to 35 μg/ml, preferably 2 to 12 μg/ml of the antibiotics is used in the method of the present invention.

The tea catechin used in the present invention is represented by structural formula (I) as shown below:

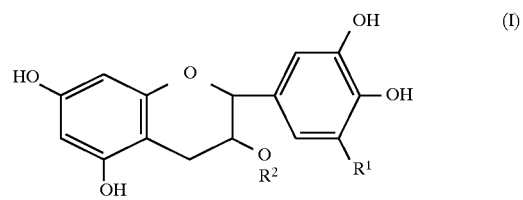

wherein $R^1$ represents H or OH and $R^2$ represents H or

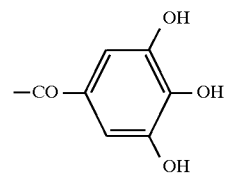

Tea catechins may be for example, (−)-epicatechin, (−)-epicatechin gallate, (−)-epigallocatechin, (−)-epigallocatechin gallate, (−)-gallocatechin etc. (inclusive of isomers thereof) and some of these catechins can be used singly or a combination of two or more compounds may be used. Among these catechins, compounds containing (−)-epicatechin gallate and/or (−)-epigallocatechin gallate are preferable. In particular, tea catechin which contains (−)-epigallocatechin gallate as its main component is desirable; for example, "Polyphenon 100"™ (product of Mitsui Norin Co. Ltd., composition: (+)-gallocatechin 1.44%, (−)-epicatechin 5.81%, (−)-epigallocatechin 17.57%, (−)-epicatechin gallate 12.51%, (−)-epigallocatechin gallate 53.9%) or "Polyphenon E"™ (product of Mitsui Norin Co. Ltd., composition: (−)-epicatechin 10.8%, (−)-epigallocatechin 9.2%, (−)-epicatechin gallate 6.5%, (−)-epigallocatechin gallate 54.8%, (−)-gallocatechin gallate 4.0%) are preferable.

The MIC of tea catechin against MRSA is 125–250 μg/ml, and in the process of the present invention, tea catechin is used in a concentration less than the MIC, and usually it is used in a concentration of about 5 to 120 μg/ml, and the most desirable concentration being 6 to 100 μg/ml.

Theaflavin used in the present invention is represented by structural formula (II) as shown below:

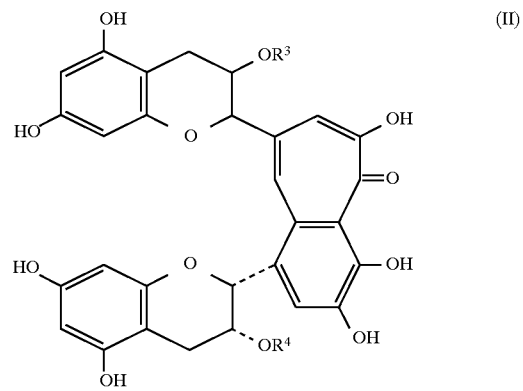

wherein $R^3$ and $R^4$ represent H or

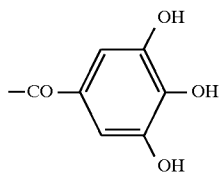

and $R^3$ and $R^4$ may be the same or different from each other.

Theaflavins may be for example, free theaflavins, theaflavin monogallate A, theaflavin monogallate B, theaflavin digallate etc. (inclusive of isomers thereof) and these theaflavins may be used singly or a combination of two or more compounds may be used. Among these theaflavins, compounds containing theaflavin digallate are preferable. In particular, the compound containing theaflavin digallate as its main component is desirable; for example "Polyphenon TF"™ (product of Mitsui Norin Co. Ltd., composition: theaflavin 16.8%, theaflavin monogallate A 19.5%, theaflavin monogallate B 16.1%, theaflavin digallate 31.4%).

The MIC of theaflavin against MRSA is 200 μg/ml, and in the process of the present invention, theaflavin is used in a concentration less than the MIC, and usually it is used in a concentration of about 5 to 100 μg/ml; the most desirable concentration being 6 to 50 μg/ml. In the process of the present invention a combination of more than two of the above mentioned tea catechins and/or theaflavins may be used.

In order to determine the proportional concentrations of tea catechins and/or theaflavins to the antibiotics, the antibacterial action of each antibiotic in the presence of 100 μg of tea catechins was measured using the cup method, and it was found that in case of 5 μg/ml of oxacillin, 12.5 μg/ml of methicillin, 32 μg/ml of aminobenzyl penicillin, 2.5 μg/ml of tetracycline and 12.5 μg/ml of chloramphenicol, there was an apparent antibacterial action against MRSA. Thus by using these amounts of antibiotics as a guide, it can be determined in what proportions to mix these two kinds of compounds.

In order to make use of the anti-bacterial action against MRSA according to the method of the present invention, antibiotics, and tea catechins and/or theaflavins are mixed in the proportions stated above and administered to patients. The mixture may be administered in various forms. For example it may be mixed with an excipient and used as an oral administration and/or non-oral administration. It may be mixed in suitable proportions with supplementary substances such as lubricating agents, emulsifying agents, dispersing agents or the like.

As an oral administration, it may be in the form of a liquid, powder, tablet, capsule, granules etc. and in such cases, the excipients used are apart from water, sugar, starch, dextran, calcium phosphate, calcium carbonate, magnesium oxide, magnesium stearate, aluminium silicate, aluminium hydroxide, sodium bicarbonate, glycerin etc.

As a non-oral administration, it may be in the form of an injection, a drip, an ointment etc. and it may be mixed with a common substance such as distilled water, physiological saline, vegetable oils such as olive oil etc., alcohol such as ethanol etc., polyethylene glycol and so on.

The present invention will be explained in detail with reference to the following examples.

EXAMPLE 1

10 strains of MRSA isolated at Showa University Hospital and 10 strains MRSA isolated at Showa University Fujigaoka Hospital were used for the following experiments. Firstly, the MIC of these bacteria was determined by the agar culture dilution method.

As a control, methicillin sensitive *Staphylococcus aureus* 209P (referred to hereinafter as MSSA) was used.

A treated agar plate (10 ml) was prepared by adding oxacillin (product of Sigma) in a final concentration of 0.25 to 1000 μg/ml and tea catechins in a final concentration of 8 to 500 μg/ml to Mueller-Hinton agar (Difco Lab. U.S.A.).

The tea catechin used was "Polyphenon 100"™ (product of Mitsui Norin Co. Ltd.).

The bacteria were cultured on the Mueller-Hinton agar plate for 20 hours and then a 1–5×10⁶/ml bacterial solution in physiological saline was prepared. 10 μl of this was spotted onto the treated agar plates of respective concentrations and cultured at 35° C. for 24 hours to determine the MIC.

Results are shown in Table 1. As is clear from the table, the MIC of tea catechin was 125 μg/ml with 6 strains, 250 μg/ml with 14 strains. On the other hand, the MIC of oxacillin was 32 μg/ml with one strain, 63 μg/ml with one strain, 125 μg/ml with 4 strains, 250 μg/ml with one strain, 500 μg/ml with 8 strains and 1000 μg/ml with 5 strains.

TABLE 1

| Strains | MIC(μg/ml) | |
|---|---|---|
| | Tea catechin | Oxacillin |
| MSSA 209P | 250 | 0.5 |
| MRSA H-5 | 125 | 500 |
| H-6 | 250 | 500 |
| H-7 | 125 | 1000 |
| H-8 | 250 | 500 |
| H-9 | 250 | 500 |
| H-13 | 250 | 125 |
| H-18 | 125 | 500 |
| H-21 | 125 | 250 |
| H-28 | 250 | 125 |
| H-29 | 250 | 63 |
| F-8 | 250 | 125 |
| F-10 | 125 | 500 |
| F-41 | 250 | 125 |
| P-49 | 250 | 500 |
| F-51 | 250 | 1000 |
| F-68 | 125 | 1000 |
| F-74 | 250 | 1000 |
| F-84 | 250 | 1000 |
| F-96 | 250 | 500 |
| F-98 | 250 | 32 |

EXAMPLE 2

The influence of tea catechins on the antibacterial action of oxacillin against MRSA was determined using the cup method. As in Example 1 the tea catechin used was "Polyphenon 100"™ (product of Mitsui Norin Co. Ltd.). Tea catechin in a concentration less than the MIC was dissolved in sterilized water and added in final concentrations of 25, 50, 100 μg/ml to a melting Mueller-Hinton agar by keeping at a temperature of 60° C. 2 ml of the Mueller-Hinton broth (Difco Lab. U.S.A.) in which test bacteria had been cultivated for 18 hours was added to 98 ml of the agar plate containing the tea catechin, and mixed well. Immediately thereafter, 10 ml samples were poured into petri dishes.

After cooling, a stainless cup (ø 8 mm) for the examination of the antibiotics was put on the agar plate in the dish, and into the cup was poured 0.1 ml of each of the various dilutions of oxacillin (5, 10, 20, 40 μg/ml), and after refrigerating for an hour, they were cultured overnight in a 36° C.

incubator and the following day the differences in inhibition (size of growth inhibition zone) were measured by slide calipers. Results are shown in FIGS. 1A to 1F, FIGS. 2A to 2F and FIG. 3. Sterilized water only was added into the cup as a control.

In the Figures, ○ indicates "Polyphenon 100" at a concentration of 100 μg/ml, ● indicates "Polyphenon 100" at a concentration of 50 μg/ml, □ indicates "Polyphenon 100" at a concentration of 25 μg/ml, ■ indicates control, i.e. no addition of "Polyphenon 100". The tested bacterial strains were resistant to oxacillin, and oxacillin up to a concentration of 40 μg/ml showed no antibacterial action as measured by the cup method.

Figure 3:
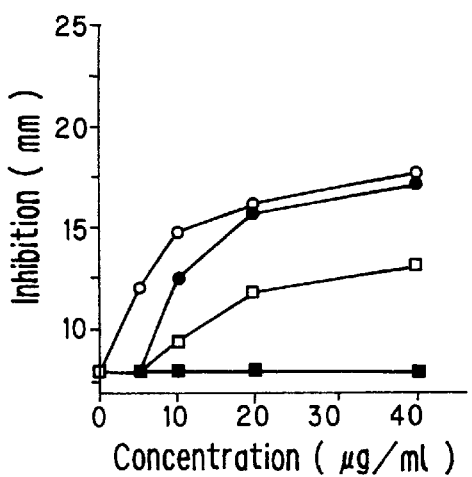
FIG. 3 is a graph which shows the synergistic effect of tea catechin (Polyphenon 100) with oxacillin against MRSA strain F-98.
Figure 4A:
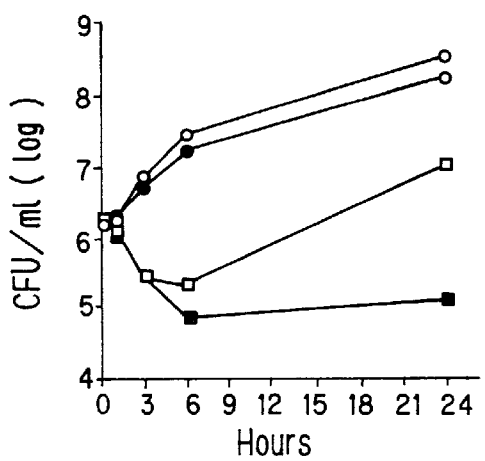
FIG. 4A is a graph which shows the synergistic effect of tea catechins (Polyphenon 100) with oxacillin against MRSA strain H-5.
Figure 4B:
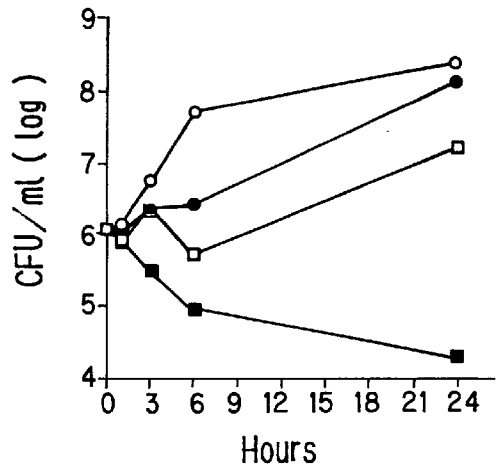
FIG. 4B is a graph which shows the synergistic effect of tea catechins (Polyphenon 100) with oxacillin against MRSA strain H-9.
Figure 4C:
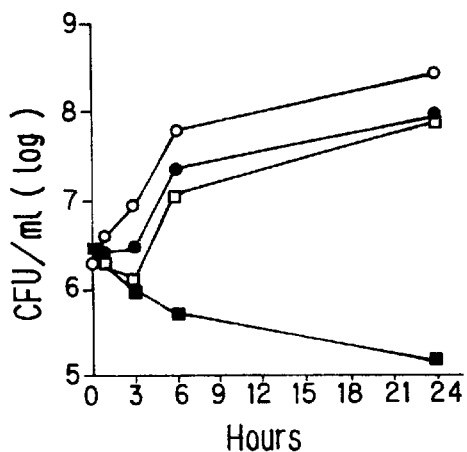
FIG. 4C is a graph which shows the synergistic effect of tea catechins (Polyphenon 100) with oxacillin against MRSA strain F-41.
Figure 4D:
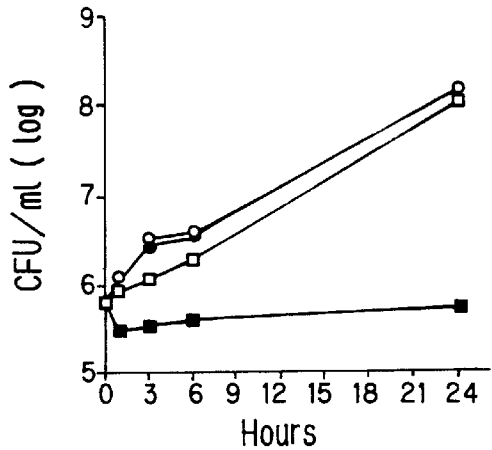
FIG. 4D is a graph which shows the synergistic effect of tea catechins (Polyphenon 100) with oxacillin against MRSA strain F-84.
Figure 5A:
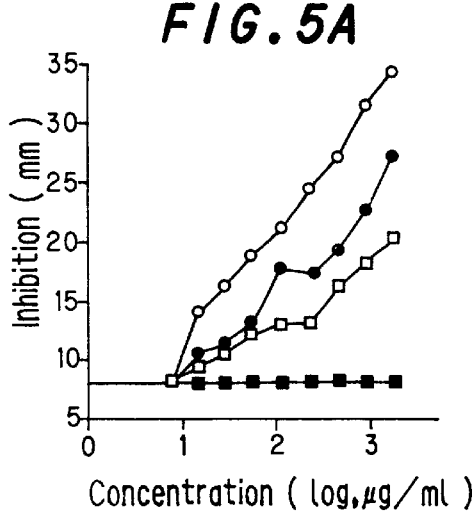
FIG. 5A is a graph which shows the synergistic effect of tea catechins (Polyphenon 100) with oxacillin against MRSA F-51.
Figure 5B:
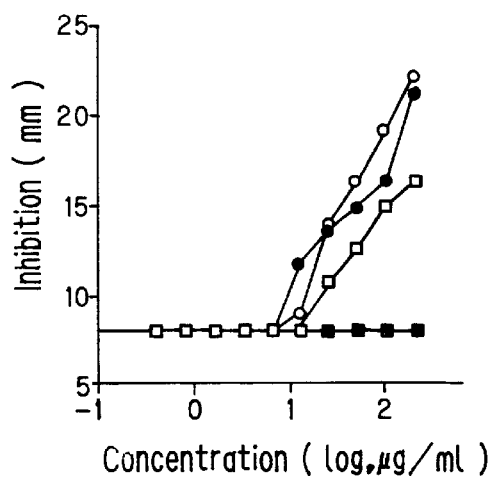
FIG. 5B is a graph which shows the synergistic effect of tea catechins (Polyphenon 100) with methicillin against MRSA F-51.
Figure 5C:
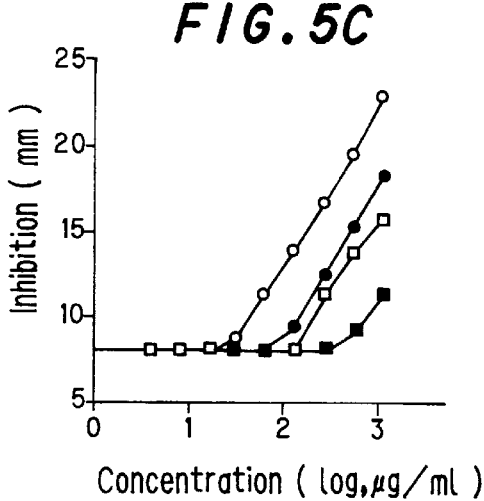
FIG. 5C is a graph which shows the synergistic effect of tea catechins (Polyphenon 100) with aminobenzyl penicillin against MRSA F-51.
Figure 5D:
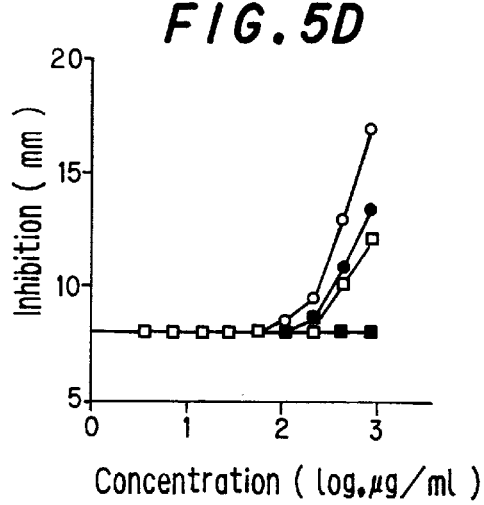
FIG. 5D is a graph which shows the synergistic effect of tea catechins (Polyphenon 100) with cephalexin against MRSA F-51.
Figure 5E:
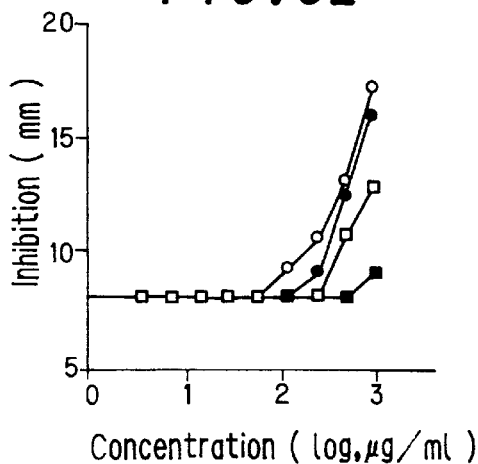
FIG. 5E shows the synergistic effect of tea catechins (Polyphenon 100) with penicillin G against MRSA F-51.
Figure 5F:
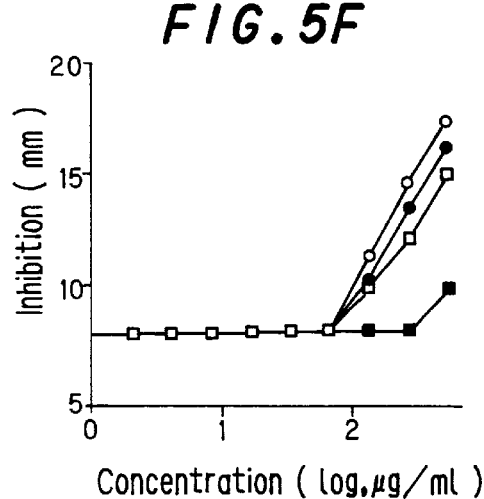
FIG. 5F is a graph which shows the synergistic effect of tea catechins (Polyphenon 100) with amikacin against MRSA F-51.

As is evident from FIGS. 1 to 3, due to the addition of tea catechins, the antibacterial activity of oxacillin against MRSA was apparent with all the bacteria tested. In particular, with the addition of 25 μg/ml of tea catechins, only 5 μg/ml of oxacillin were required to show an antibacterial action against MRSA strains H-5, H-8, F-49, F-68, F-74.

Moreover, with the addition of 10, 20, 40 μg/ml of oxacillin, the size of the growth inhibition zone increased according to the oxacillin concentration. Also when the amount of tea catechins was increased to 50 μg/ml or 100μg/ml, there was an even greater enlargement of the growth inhibition zone, proving the dose-dependency.

EXAMPLE 3

The influence of tea catechins on the antibacterial action of oxacillin against MRSA was determined by counting the viable cells at intervals as described above. In this case, also the tea catechin used was "Polyphenon 100" (product of Mitsui Norin Co. Ltd.).

The test bacteria which had been incubated for 18 hours in Mueller-Hinton agar was scraped with a platinum needle and a bacterial solution $10^6$ cfu/ml was prepared with physiological saline. A denary dilution of the above solution was made using a two-fold Mueller-Hinton broth (Difco Lab. U.S.A.) to which $Ca^{2+}$ 25 mg/liter, $Mg^{2+}$ 12.5 mg/liter were added in order to increase the sensitivity of the assay and the stability of the antibiotics.

To this bacterial solution, tea catechins were added to make the final concentration 100 μg/ml and oxacillin was added to make a final concentration of 5 μg/ml. After mixing well, the number of viable cells were counted at intervals of 1, 3, 6 and 24 hours.

Results are shown in FIGS. 4A to 4D. Results of the control group without the addition of the antibiotics and the groups where two compounds were used independently are also shown in FIG. 4A to 4D. In the Figures, ○ represents the control group, ● represents the group to which 5 μg/ml of oxacillin only was added, □ represents the group to which 100 μg/ml of "Polyphenon 100" only was added, and ■ represents the group to which 5 μg/ml of oxacillin and 100 μg/ml of "Polyphenon 100" were added.

The group to which oxacillin only was added, showed a growth curve similar to that of the control. In the group to which tea catechin only was added, there were some bacterial strains which at one point showed a decrease in the number of viable cells, but after that there was an increase. In the group where tea catechin was combined with oxacillin at a concentration which independently showed no antibacterial action, oxacillin showed an antibacterial action on all of the bacteria. When the viable cells were counted after 24 hours, compared with the control, H-5 was about 1/1000 and H-9, F-41, F-84 strains were about 1/1000–1/10000.

EXAMPLE 4

The influence of tea catechins on the antibacterial effect of oxacillin on MRSA was investigated using the cup method as described in Example 2 and the results are shown in FIGS. 5A–5F and FIGS. 6A–6C.

Figure 6A:
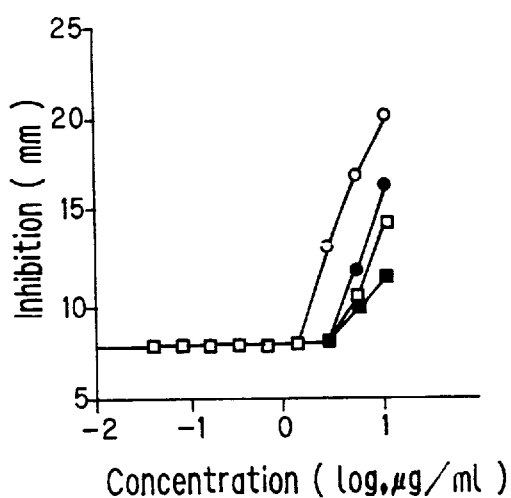
FIG. 6A is a graph which shows the synergistic effect of tea catechins (Polyphenon 100) with tetracycline against MRSA F-51.
Figure 6B:
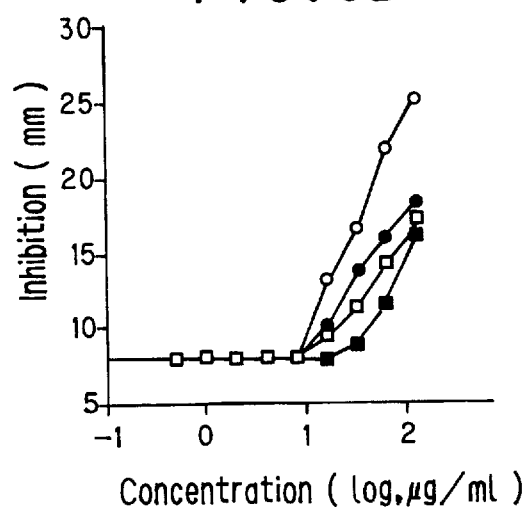
FIG. 6B is a graph which shows the synergistic effect of tea catechins (Polyphenon 100) with chloramphenicol against MRSA F-51.
Figure 6C:
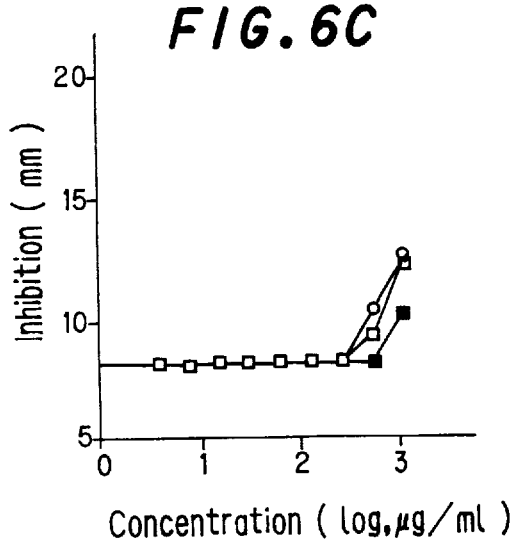
FIG. 6C is a graph which shows the synergistic effect of tea catechins (Polyphenon 100) with gentamicin against MRSA F-51.

F-51, a strain of bacteria with a high resistancy against oxacillin was used and the tea polyohenols used were in the form of Polyphenon 100 (Mitsui Norin Co. Ltd.). The antibiotics used were oxacillin (Sigma Chemical Company) (FIG. 5A), methillicin (Sigma Chemical Company)(FIG. 5B), aminobenzyl penicillin(Ban-yu Pharmaceutical Co. Ltd.) (FIG. 5C), cephalexin (Wako Pure Chemical Industries)(FIG. 5D), penicillin G (Meiji Pharmaceutical Co. Ltd.)(FIG. 5E), amikacin (Ban-yu Seiyaku)(FIG. 5F), tetracycline (Wako Pure Chemical Industries )(FIG. 6A), chloramphenicol (Wako Pure Chemical Industries )(FIG. 6B), gentamicin (Wako Pure Chemical Industries )(FIG. 6C).

In the figure, ○ indicates Polyphenon 100 at a concentration of 100 μg/ml, ● indicates Polyphenon 100 at a concentration of 50 μg/ml, □ indicates Polyphenon 100 at a concentration of 25 μg/ml, ■ indicates the control containing no Polyphenon 100.

As is evident from this figure, under the cup method F-51 strain showed resistancy with up to 2000 μg/ml oxacillin, but when 25 μg/ml of Polyphenon 100 was added to the culture, oxacillin showed an antibacterial action at 10 μg/ml, and the size of the growth inhibition zone depended on the concentration.

In the same way, the synergistic effect of methicillin, aminobenzyl penicillin, cephalexin, penicillin G i.e. β-lactums, was confirmed. Amikacin, tetracycline, chloramphenicol also showed a synergistic effect but the antibacterial effect of gentamicin with the addition of tea catechins was low. F-51 was susceptible to vancomycin but the antibacterial activity was not influenced by the addition of tea catechins.

EXAMPLE 5

Figure 7:
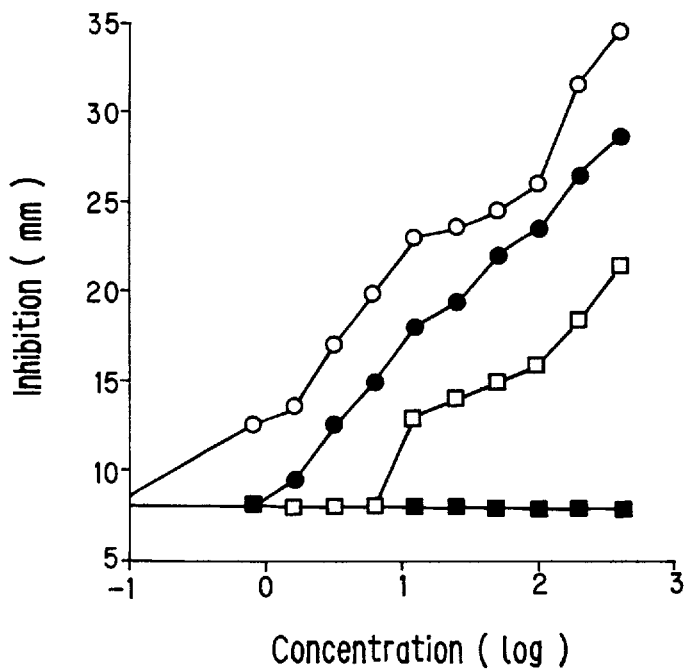
FIG. 7 is a graph which shows the synergistic effect of epicatechin gallate with oxacillin against MRSA F-51.
Figure 8:
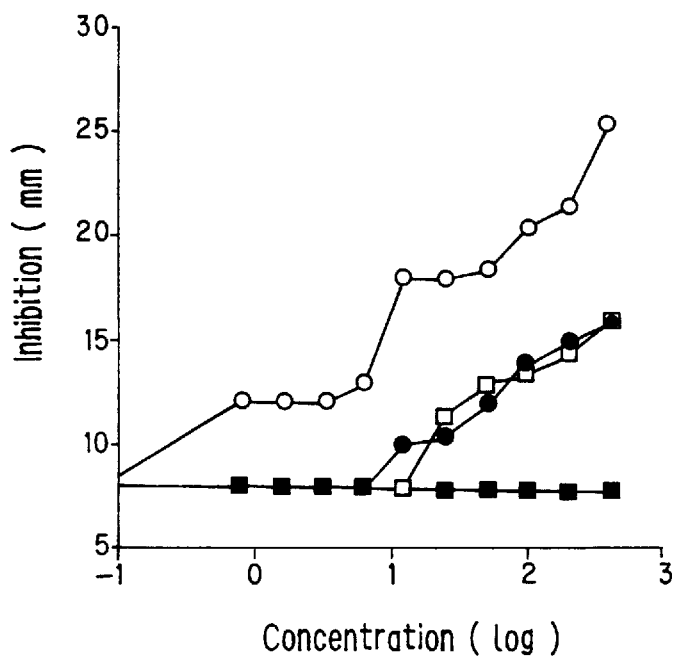
FIG. 8 is a graph which shows the synergistic effect of epigallocatechin gallate with oxacillin against MRSA F-51.
Figure 9:
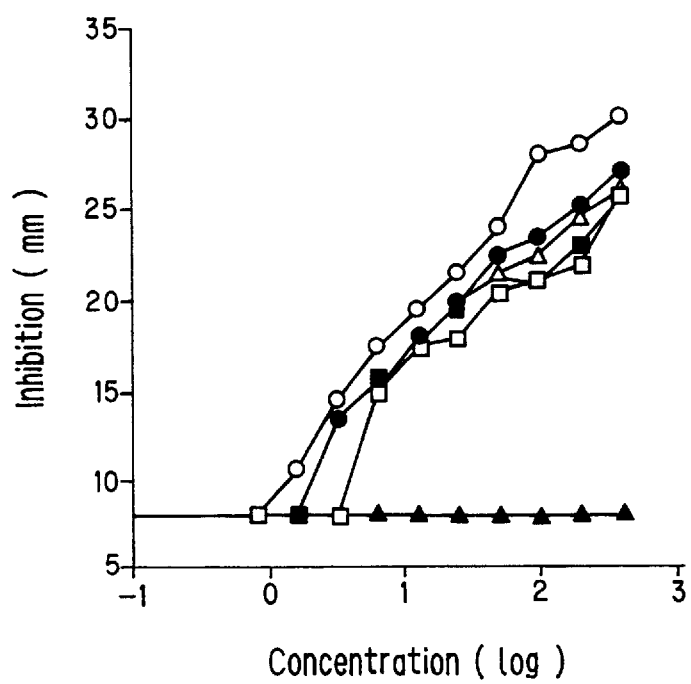
FIG. 9 is a graph which shows the synergistic effect of theaflavin digallates with oxacillin against MRSA F-51.
Figure 10A:
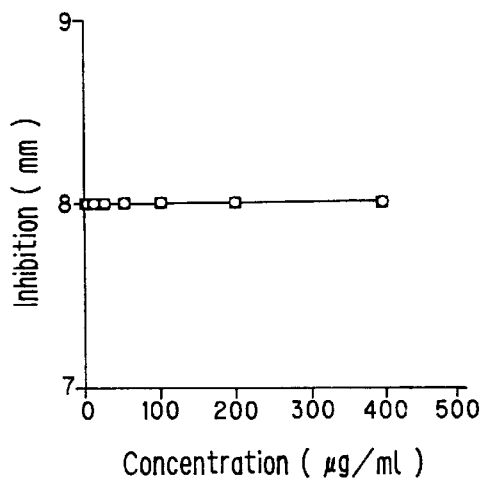
FIG. 10A is a graph which shows the ineffectiveness of tea catechins ((-)-epigallocatechin gallate) with kanamycin against MRSA F-51.
Figure 10B:
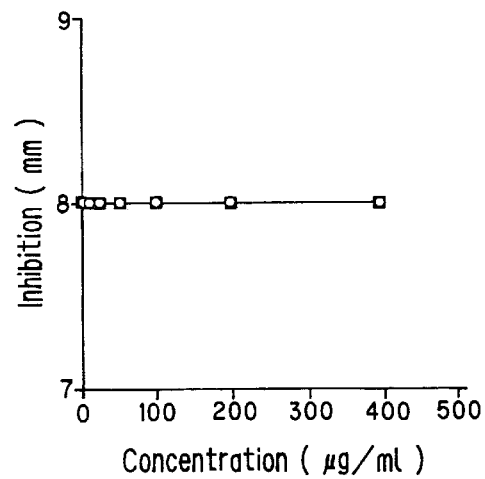
FIG. 10B is a graph which shows the ineffectiveness of tea catechins ((-)-epigallocatechin gallate) with erythromycin against MRSA F-51.
Figure 10C:
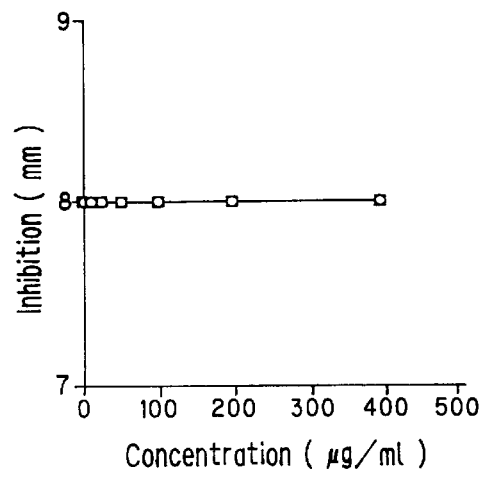
FIG. 10C is a graph which shows the ineffectiveness of tea catechins ((-)-epigallocatechin gallate) with climdamycin against MRSA F-51.
Figure 10D:
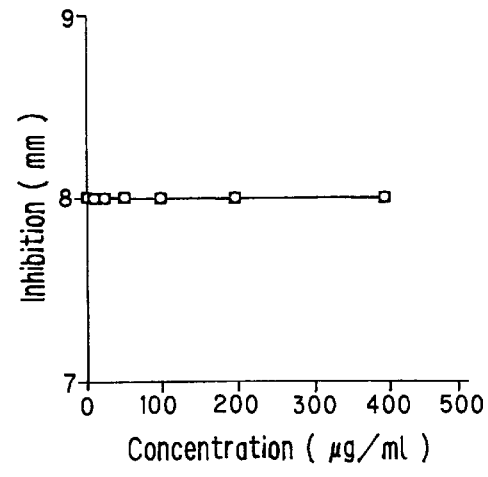
FIG. 10D is a graph which shows the ineffectiveness of tea catechins ((-)-epigallocatechin gallate) with colistin against MRSA F-51.

The influence of individual pure catechins and a pure theaflavin on the antibactial effect of oxacillin on MRSA was determined by the cup method as in Example 2, and the results are shown in FIGS. 7–9.

The strain of bacteria F-51, which has high resistancy to oxacillin was used, and tea catechins and theaflavins used were (+)-gallocatechin, (−)-epicatechin, (−)-epigallocatechin, (−)-epicatechin gallate, (−)-epigallocatechin gallate and theaflavin digallates. Oxacillin (Sigma Chemical Co.) was used as antibiotic.

In FIG. 7, ○ indicates (−)-epicatechin gallate at a concentration of 25 μg/ml, ● indicates a concentration of 12.5 μg/ml, □ indicates a concentration of 6.3 μg/ml, and ■ indicates no addition of (−)-epicatechin gallate.

In FIG. 8, ○ indicates (−)-epigallocatechin gallate at a concentration of 50 μg/ml, ● indicates a concentration of 25 μg/ml, □ indicates a concentration of 12.5 μg/ml, ■ indicates a concentration of 6.3 μg/ml, and Δ indicates no addition of (−)-epigallocatechin gallate.

In FIG. 9, ○ indicates theaflavin gallate at a concentration of 100 μg/ml, ● indicates a concentration of 50 μg/ml, □ indicates a concentration of 25 μg/ml, ■ indicates a concentration of 12.5 μg/ml, Δ indicates a concentration of 6.3 μg/ml, and ▲ indicates no addition of theaflavin gallate.

The addition of (+)-gallo-catechins up to a concentration of 800 μg/ml to 40 μg/ml oxacillin showed no antibacterial effect. In the same way the addition of (−)-epicatechin up to a concentration of 100 μg/ml, or (−)-epigallocatechin up to a concentration of 50 μg/ml showed no antibacterial effect.

On the other hand, as is shown in FIGS. 7–9, with (−)-epicatechin gallate, (−)-epigallocatechin gallate and theaflavin digallates an antibacterial effect was apparent. These results show that the galloyl moiety of catechins and theaflavins is crucial to their synergistic effects with antibiotics.

COMPARATIVE EXAMPLE

This experiment was carried out in the same way as in Example 4 except that the following antibiotics were used: kanamycin (Wako Pure Chemicals), erythromycin (Wako Pure Chemicals), climdamycin (Sigma Chemnical Company), and colistin (Wako Pure Chemicals) and the effect of each catechin on the antibacterial action of each antibiotic was investigated by the cup method as in Example 2.

Results obtained are shown in FIGS. 10A–D. F-51 strain which showed a high resistancy to oxacillin was used as the test bacteria and (−)-epigallocatechin gallate was used as the tea catechin. In the figure, ○ indicates (−)-epigallocatechin gallate at a concentration of 50 μg/ml, ● indicates (−)-epigallocatechin gallate at a concentration of 25 μg/ml, □ indicates (−)-epigallocatechin gallate at a concentration of 12.5 μg/ml, ■ indicates (−)-epigallocatechin gallate at a concentration of 6.3 μg/ml, and Δ indicates no addition of (−)-epigallocatechin gallate.

As is evident from the figure, under the cup method F-51 strain showed its resistancy with up to 400 μg/ml of each of the antibiotics, and no improved synergistic antibacterial effects could be observed even though (−)-epigallocatechin was added at any concentration and combined with the antibiotics, and there was no change in the size of the inhibition zone.

What is claimed is:

1. In an improved antibiotic composition against methicillin resistant *Staphylococcus aureus* having increased antibiotic activity, the improvement comprising said antibiotic being in combination with at least one catechin of the following formula (I):

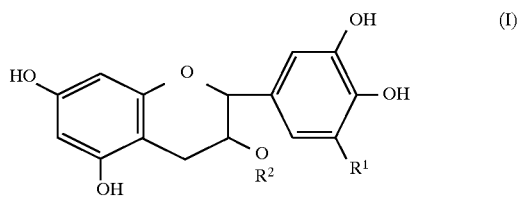

wherein $R^1$ represents H or OH and $R^2$ represents H or

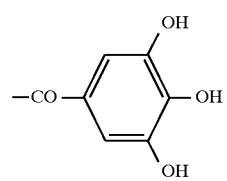

said antibiotic being selected from the group consisting of oxacillin, methicillin, aminobenzyl penicillin, tetracycline, chloramphenicol, cephalexin, penicillin G and amikacin, and said antibiotic and said at least one catechin being in amounts to provide effective antibiotic activity.

2. The antibiotic composition according to claim 1, wherein the amount of the antibiotic is 2–35 μg/ml and the amount of the catechin is 20–120 μg/ml.

3. The antibiotic composition according to claim 1, wherein the antibiotic is oxacillin, the oxacillin being in an amount of 5 μg/ml and the catechin being in an amount of 100 μg/ml.

4. The antibiotic composition according to claim 1, wherein the antibiotic is methicillin, the methicillin being in an amount of 12.5 μg/ml and the catechin being in an amount of 100 μg/ml.

5. A method of increasing the activity of an antibiotic composition against methicillin resistant *Staphylococcus aureus* comprising adding to said antibiotic, at least one catechin of the following formula (I):

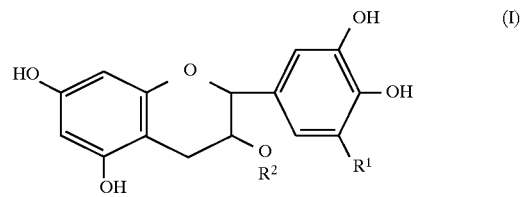

wherein $R^1$ represents H or OH and $R^2$ represents H or

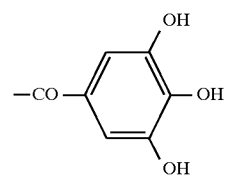

said antibiotic being selected from the group consisting of oxacillin, methicillin, aminobenzyl penicillin, tetracycline, chloramphenicol, cephalexin, penicillin, and amikacin, and said antibiotic and said at least one catechin being in amounts to provide effective antibacterial activity.

6. The method according to claim 5, wherein said antibiotic is in an amount of 2 to 35 μg/ml.

7. The method of claim 6, wherein said at least one catechin is in an amount of 5 to 120 μg/ml.

8. The method according to claim 5, wherein said antibiotic is in an amount of 2 to 12 μg/ml.

9. The method according to claim 8, wherein said at least one catechin is in an amount of 6 to 100 μg/ml.

10. The method according to claim 9, wherein said at least one polyphenol is selected from the group consisting of (−)-epicatechin gallate, and (−)-epigallocatechin gallate.

11. The method according to claim 5, wherein said at least one catechin is a catechin having a galloyl moiety.

12. The method according to claim 5, wherein said antibiotic is in an amount such that it would not be effective against methicillin-resistant *Staphylococcus aureus* without said at least one catechin.

13. The method according to claim 5, wherein the at least one catechin is a catechin selected from the group consisting of epicatechin gallate and epigallocatechin gallate.

14. The method according to claim 5, wherein the at least one catechin is a catechin composition which has as its main component epigallocatechin gallate.

* * * * *